United States Patent [19]
Crankshaw

[11] Patent Number: 5,409,456
[45] Date of Patent: Apr. 25, 1995

[54] METHOD FOR INTRAVENOUS DRUG INFUSION

[75] Inventor: David P. Crankshaw, Toorak, Australia

[73] Assignee: The University of Melbourne, Australia

[21] Appl. No.: 204,346

[22] PCT Filed: Sep. 11, 1992

[86] PCT No.: PCT/AU92/00485

§ 371 Date: Jul. 7, 1994

§ 102(e) Date: Jul. 7, 1994

[87] PCT Pub. No.: WO93/04713

PCT Pub. Date: Mar. 18, 1993

[30] Foreign Application Priority Data

Sep. 11, 1991 [AU] Australia ............... PK8315

[51] Int. Cl.⁶ ............... A61M 31/00; A61M 37/00
[52] U.S. Cl. ................... 604/50; 604/154; 604/67; 128/DIG. 13
[58] Field of Search .................... 604/49–53, 604/65–67, 154, 155; 128/DIG. 1, DIG. 13

[56] References Cited

U.S. PATENT DOCUMENTS

| | | | |
|---|---|---|---|
| 3,809,871 | 5/1974 | Howard et al. | |
| 4,502,488 | 3/1985 | Degironimo et al. | |
| 4,741,732 | 5/1988 | Crankshaw et al. | 604/50 |
| 4,880,014 | 11/1989 | Zarowitz et al. | 604/50 |
| 5,034,004 | 7/1991 | Crankshaw | 604/67 |
| 5,254,087 | 10/1993 | McEwen | 604/66 |

FOREIGN PATENT DOCUMENTS

| | | |
|---|---|---|
| 420198/85 | 11/1985 | Australia . |
| 364010 | 4/1990 | European Pat. Off. . |
| 497041 | 8/1992 | European Pat. Off. . |
| 2603488 | 3/1988 | France . |
| 84/00894 | 5/1974 | WIPO . |
| 85/02546 | 6/1985 | WIPO . |

OTHER PUBLICATIONS

International Search Report dated Nov. 10, 1992 for PCT/AU92/00485.

Primary Examiner—John D. Yasko
Assistant Examiner—Frank Wilkens, III
Attorney, Agent, or Firm—Andrus, Sceales, Starke & Sawall

[57] ABSTRACT

A method and system for the infusion of a drug into a patient involving: (i) calculating a multiplicity of infusion rate profiles for a selected drug by monitoring drug efflux from the body of a group of patients for a corresponding multiplicity of target concentrations of the selected drug; (ii) determining the body size of the patient, such as their Lean Body Mass; (iii) selecting a target concentration of the drug to, in turn, cause selection from the multiplicity of infusion rate profiles of an infusion rate profile substantially corresponding to the infusion rate profile for the selected target concentration; (iv) scaling the selected infusion rate profile by the determined body size or Lean Body Mass of the patient; and (v) administering the drug to the patient in accordance with the scaled profile by means of an infusion device which is controlled to deliver said drug at said scaled infusion rate profile. By using the aforesaid method and system, drugs which are non-linear in their effect on a patient are able to be delivered to the patient in a much more accurate manner thereby avoiding overdosing or underdosing of the drug and the undesirable consequences thereof.

9 Claims, 1 Drawing Sheet

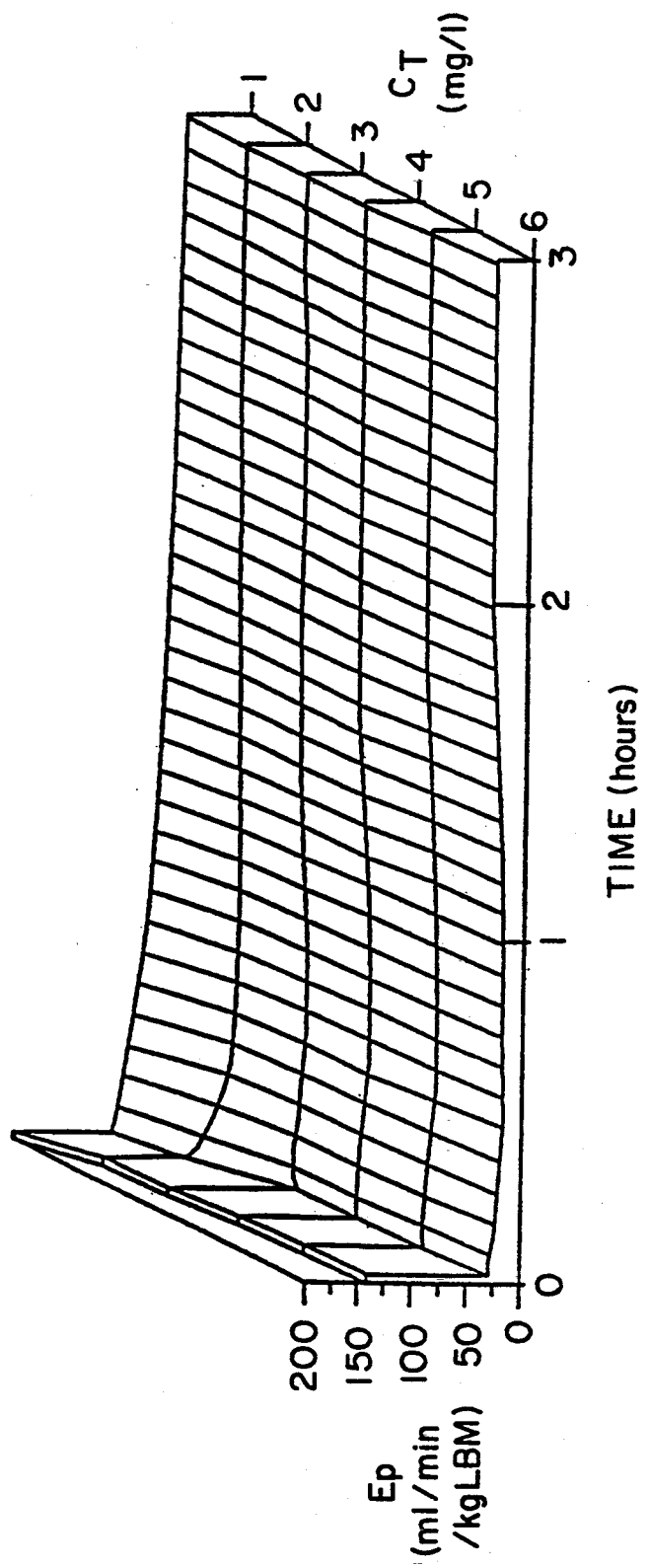

METHOD FOR INTRAVENOUS DRUG INFUSION

FIELD OF THE INVENTION

This invention relates to a method and device for the precise dosing of intravenously administered drugs and in particular anaesthetic agents.

BACKGROUND OF THE INVENTION

Precision in dosing infused anaesthetic agents has the advantage of providing adequate operating conditions in each patient, avoiding unwanted unconsciousness in sedated patients, avoiding respiratory arrest and severe hypotension in anaesthetized patients and particularly, avoiding awareness where unconsciousness is desired. The conventional approach to determining the bolus and variable infusion rate required to achieve a nominated target blood level is to derive a compartmental pharmacokinetic model following the administration of a single dose.

In U.S. Pat. No. 4,741,732 to Crankshaw et al and Austrailian Patent No. AU-B-42019/85 to The University of Melbourne the entire contents of both documents being hereby incorporated by cross-reference, there is described a plasma drug efflux method to determine infusion rates of a given drug to achieve a constant concentration necessary to achieve an effect in the patient. The present applicant has shown for a number of drugs that the infusion rate required to achieve a therapeutic effect differs to a considerable extent from the prediction made from giving a single dose of each of these drugs. there is also described in subsequent U.S. Pat. No. 5,034,004 Crankshaw et al improvements in a device to administer drugs intravenously, particularly during anaesthesia.

In summary, the disclosures of U.S. Pat. No. 4,441,732 and Australian Patent 42019/85 show that:
1. The rate of elimination of drugs from the blood is expressed as the volume of blood from which drug is removed each minute (liters/minute), and varies with time as it depends on the rate of elimination from the body plus the accumulation of drug in the body.
2. The rate of elimination modified by the presence of the drug which influences both the elimination and the accumulation of the drug.
3. The net effect of all these factors is a time varying measure of the rate of removal of the drug we term Plasma Drug Efflux (Ep).
4. Ep is determined at a single drug concentration. This concentration is chosen as the mid-point within the range of concentrations normally used during anaesthesia.
5. To maintain a specific target concentration (Ct) of the drug, the expected rate of loss of drug from the circulation is calculated by multiplying Ep (litres/min) by Ct (mg/liter),
6. The rate of loss (Q mg/min) equals the rate at which drugs must be administered to maintain to constant concentration, and as Ep varies with time, Q varies with time in direct proportion.
7. The value of Ep is stored in the control system of the syringe pump as a single infusion rate profile for each drug to permit the generation of Q for each value of Ct.

Since this original disclosure, the applicant has noted that, for anaesthetic agents, a number of concentrations can be defined which produce different therapeutic effects, for example:

(a) sedation where the subject is drowsy but not fully unconscious (b) lightly anaesthetized where another drug such a nitrous oxide is required to achieve complete anaesthesia (c) moderately anaesthetized when the drug alone produces anaesthesia (d) deeply anaesthetized when the high concentration of the drug is used to achieve effects as well as anaesthesia, such as lowering of the arterial blood pressure or protection of the brain from lack of oxygen.

When evaluating the ability to implement plasma drug efflux rate profiles obtained according to the method of U.S. Pat. No. 4,471,732 at a number of different desired or target concentrations ($C_T$), the applicant has found, particularly with the anaesthetic agent propofol, that the infusion rates required to maintain a constant concentration at each of these different clinically useful concentrations are not in direct proportion to each other. Thus as a result of observation of the method of the U.S. patent it has been determined that Ep during sedation for light anaesthesia, average anaesthesia and deep anaesthesia, does not remain constant in the case of Propofol, and both the size and the shape of the Ep curve varies for different levels of anaesthesia. This new observation that Ep is concentration dependant and that the simple proportion described in the U.S. patent does not apply means that in the case of propofol the amount of blood from which drug is removed actually falls as the concentration of the drug increases. The magnitude of this fall is such that Ep determined during sedation is approximately twice that determined during average anaesthesia, so that if a single Ep curve, determined during sedation, were used to calculate the infusion rate for average anaesthesia, an infusion rate of close to 100% higher than required to maintain Ct could result and overdose would occur. Similarly, if the Ep curve, determined during average anaesthesia, were used to generate the infusion rate to achieve sedation the infusion ration would be half that required and inadequate drug effect would result. As well, for a given value of Ct the presence of the anaesthetic nitrous oxide reduces the values of Ep when compared with the absence of nitrous oxide.

To summarize the above while the method of proportional adjustment of the infusion rate (U.S. Pat. No. 4,741,732, FIG. 7 ) is suitable for a number of agents, it is not suitable for adjusting the target concentration of drugs where non-linearity is apparent. Similarly, the required rate of infusion at any of these clinically useful concentrations may be altered considerably if a second anaesthetic agent, such as nitrous oxide is given at the same time. This observation means that if, for example nitrous oxide is added to the patient or removed at any time an adjustment must be made in the infusion rate profile to account for this.

While the invention is most preferably used with the drug efflux method of drug infusion profile generation described in U.S. Pat. No. 4,741,732, it is equally applicable to other methods of generating similar, albeit less effective, profiles. For example, it is possible to produce a family of profiles similar to the profiles produced by the method of the above U.S. patent by using a multi-compartment pharmaco-kinetic model used in the papers by Kruger-Theimer, and the other authors referred to in the introduction of the above U.S. patent, and manipulating the parameters of the model until profiles bearing some similarity to those produced by the method of the above U.S. patent are produced.

SUMMARY OF THE INVENTION

In accordance with the invention, there is provided a method of infusion of an anaesthetic agent into a patient comprising the steps of:
(i) calculating a multiplicity of infusion rate profiles for a selected agent by monitoring drug efflux from the body of a group of patients for a corresponding multiplicity of target concentrations of the selected agent, said multiplicity of infusion rate profiles including at least a set of profiles which cause the induction of light, average and deep anaesthesia in the patient,
(ii) determining the body size of the patient, such as their Lean Body Mass;
(iii) selecting a target concentration of the agent to in turn cause selection from the multiplicity of infusion rate profiles an infusion rate profile substantially corresponding to the infusion rate profile for the selected target concentration;
(iv) scaling the selected infusion rate profile by the determined body size or Lean Body Mass of the patient, and
(v) administering the agent to the patient in accordance with the scaled profile by means of an infusion device which is controlled to deliver said agent at said scaled infusion rate profile.

In a preferred form of the invention, said profile is determined by:
(a) infusing a drug at arbitrary but known rates into a group of patients for each of whom the Lean Body Mass has been determined;
(b) determining the plasma arterial concentration of the drug in each patient at a number of specific time intervals throughout each infusion period;
(c) for each patient, estimating the rates of loss of drug from the circulation at a number of specific time instants by dividing the known infusion rates per Lean Body Mass of these instants by the plasma arterial concentrations of the drug at each of these instants;
(d) calculating the average of the estimated rates of loss of drug from the circulation per Lean Body Mass unit at each specific time interval for the group of patients;
(e) interpolating the successive average points between the specific time intervals to produce an infusion profile;
(f) infusing said drug in accordance with said infusion profile determined from said interpolations into a group of patients for each of whom the Lean Body Mass has been determined, said infusion rate being scaled according to said Lean Body Mass of each patient, and
(f) repeating steps (b) to (f) until a desired steady plasma arterial content of the drug is substantially maintained throughout the infusion period.

The invention also provides an infusion system for regulating the delivery of an anaesthetic agent to a patient, including control means for controlling the operation of an infusion pump, said control means including pre-programmed means for varying the infusion rate with respect to elapsed time, said pre-programmed means being programmed with a multiplicity of infusion rate profiles which have been determined by a drug efflux method, and which correspond to a multiplicity of target concentrations of the agent, said multiplicity of infusion rate profiles including at least a set of profiles which cause the induction of light, average and deep anaesthesia in the patient, scaling means for setting the body size or Lean Body Mass of the patient, means for selecting a target concentration to cause selection of the corresponding infusion rate profile so that the pre-programmed means varies the infusion rate in accordance with the corresponding drug infusion rate profile, said scaling means causing modification of the selected pre-programmed infusion rate profile by a fixed proportion over each time period of operation of said infusion pump.

The predetermined drug delivery rate profiles are preferably stored in a data storage and processing device which controls said infusion device at a rate which is subjected to said scaling. In one form, the data storage and processing device is a programmable read only memory and microprocessor which control said infusion device.

Where the drug under consideration is an anaesthetic agent, the multiplicity of infusion rate profiles includes at least a set of profiles which cause the induction of light, average and deep anaesthesia in the patient.

In a particularly preferred form of the invention, the method further includes the storage in the storage and processing device of a further multiplicity of similarly determined infusion rate profiles where an anaesthetic agent such as nitrous oxide has been used in addition to the selected anaesthetic to induce the desired level of anaesthesia, and selecting one of the profiles where said another agent such as nitrous oxide is used to achieve anaesthesia in the patient.

The invention also provides an infusion system for regulating the delivery of a drug to a patient, including control means for controlling the operation of an infusion pump, said control means including pre-programmed means for varying the infusion rate with respect to elapsed time, said pre-programmed means being programmed with a multiplicity of infusion rate profiles which have been determined by a drug efflux method, and which correspond to a multiplicity of target concentrations of the drug, scaling means for setting the body size or Lean Body Mass of the patient, means for selecting a target concentration to cause selection of the corresponding infusion rate profile so that the pre-programmed means varies the infusion rate in accordance with the corresponding drug infusion rate profile, said scaling means causing modification of the selected pre-programmed infusion rate profile by a fixed proportion over each time period of operation of said infusion pump.

In a preferred form, the system is substantially as described in U.S. Pat. No. 4,741,732 or in U.S. Pat. No. 5,034,004, except that the pre-programmed means is programmed with said multiplicity of infusion rate profiles as defined above.

Where the target concentration of the drug does not substantially correspond to the target concentration used to generate a particular infusion rate profiles, an appropriate infusion rate value is calculated by interpolation from the infusion rate profiles closest to the selected target concentration of the drug, and infusion of the drug proceeds at that infusion rate until a further interpolated infusion rate needs to be calculated to achieve the desired target concentration of the drug.

By generating a new drug infusion rate profile which is correct for the new target concentration, the newly set concentration is rapidly achieved thereby avoiding overdosing at higher concentrations and underdosing at lower concentrations.

With the simplicity of the efflux approach, and the possibility of defining average infusion rates at various target concentrations, a three dimensional profile is able to be constructed with representative values stored in the read only memory (ROM) of the infusion device to cover values of $C_T$ ranging from light sedation to deep anaesthesia levels.

BRIEF DESCRIPTION OF THE DRAWING

The foregoing and other features objects and advantages of the present invention will become more apparent from the following description of the preferred embodiments and accompanying drawing in which the single figure is a three dimensional diagram of a matrix of typical plasma drug efflux profiles for different target concentrations of the intravenous anaesthetic agent propofol.

DESCRIPTION OF PREFERRED EMBODIMENT

The FIGURE is a diagram of plasma drug efflux profiles of propofol necessary to achieve a number of different target concentrations and hence different anaesthetic effects. During sedation, where a target concentration of 1 mg/liter would be appropriate, the infusion rate profile closely approaches the prediction from a single dose model (see U.S. Pat. No. 4,741,732), but at deep anaesthetic levels (6 mg/litre), the required plasma drug efflux rate profile is proportionately less and of a different shape. Between these extremes are various plasma drug efflux rate profiles determined according to the method of U.S. Pat. No. 4,741,732 or some equivalent method which are required to maintain each of the nominated values of $C_T$. We have also found that, when a second agent such as the gas nitrous oxide is given to the patient, at a usual concentration of 50% to 70% of the total gas concentration breathed by the patient, the plasma efflux rate profiles determined by the method of U.S. Pat. No. 4,741,732 or some equivalent method to achieve a given concentration of propofol are reduced by approximately 30% and have a different shape.

The applicant considers that a clinically useful infusion device, particularly for the anaesthetic agent propofol, will have stored in the ROM of the infusion device, such as is described in U.S. Pat. Nos. 4,741,732 and 5,034,004, not one plasma drug efflux rate profile stored for each drug, but a number of infusion profiles which are representative of a range of clinically useful target arterial blood concentrations (see Figure). for example, a set of plasma drug efflux rate profiles, determined for various target concentrations of propofol, such as 1, 3, 5 and 9 mg/l, in patients also receiving 100% oxygen, could be stored in ROM, together with another set of plasma drug efflux rate profiles, determined at various target concentrations, such as 2, 4 and 6 mg/l, in patients who were receiving say 60% nitrous oxide in oxygen in the inhaled gases. These plasma drug efflux rate profiles could also have been determined by some rules other than the plasma drug efflux method described in the aforementioned U.S. patent or by some substantially equivalent means, as referred to earlier.

Once the target concentration is entered the operator will be prompted by devices of the type described in the above U.S. patents to enter whether nitrous oxide is being used. If the nominated target concentration is for example 1, 3, 5 or 9 mg/l, and a plasma drug efflux rate profile is stored for that concentration, that plasma drug efflux profile will be used to control the infusion of the drug according to the method described in U.S. Pat. No. 4,741,732. If an entry is made that nitrous oxide is being used and the nominated target concentration is for example 2, 4 or 6 mg/l, and a plasma drug efflux rate profile determined for one of those concentrations in the presence of nitrous oxide is present, it will be followed.

If the operator nominates a target concentration other than one of the specific concentrations for which a plasma drug efflux rate profile is stored, with or without nitrous oxide, the rate of infusion will be calculated by interpolation from the plasma drug efflux rate profile stored for a target concentration immediately above and from the plasma drug efflux rate profile stored for a target concentration immediately below at each instant in time. An imaginary line will be drawn, at each time interval, between the rate stored above and the rate stored below. Then the proportional rate at the intermediate target concentration will be calculated. A new rate profile will result, which is suitable for the new target concentration and his will then be multiplied by the new target concentration, the lean body mass or some other measure of patient size, and the result used to control the delivery of the drug as disclosed in U.S. Pat. Nos. 4,741,732 or 5,034,004.

By way of example, if the Plasma Drug Efflux value is determined at 15 minutes for a target concentration of 3 mg/l is 0.100 ml/min/kgLBM (See FIG. 1) and at the same time the plasma Drug Efflux value determined for a target concentration of 5 mg/l is 0.075 ml/min/kgLBM then the derived Plasma Drug Efflux value at the same time, for an intermediate a target concentration of 3.5 mg/l, is given by:

$$\text{Efflux} = 0.100 + ((0.075 - 0.100) \times ((3 - 3.5)/(3 - 5)))$$
$$= 0.100 - 0.006$$
$$= 0.094 \text{ ml/min/kg} LBM$$

Then, for the target concentration of 3.5 mg/l in a patient of lean mass of 50 kg the actual infusion rate of administration of propofol at that time is found by $$\text{Rate} = 0.0938 \times 3.5 \times 50$$
$$= 16.40 \text{ mg/min.}$$

If the operator during operation changes to a new value of the target concentration then the calculation will proceed according to the new value. If the new target concentration is outside the target concentrations of the plasma drug efflux rate profiles used previously, a new pair of plasma drug efflux rate profiles will be substituted.

If the operator, during operation, adds nitrous oxide to the patient, an entry will be made in the control panel of the infusion device to this effect. Following this entry the infusion device will then follow the plasma drug efflux rate profile derived when nitrous oxide was present or an intermediate value, calculated as described above. If a change is made from using nitrous oxide to not using nitrous oxide the infusion device will then follow the set of plasma drug efflux rate profiles determined when nitrous oxide was not in use.

While the above description relates to propofol, the invention is equally applicable to other anaesthetic agents and to other drugs capable of having their efflux profiles determined as defined above or by other methods known in the art.

I claim:

1. A method of infusion of an anaesthetic agent into a patient comprising the steps of:
   (i) calculating a multiplicity of infusion rate profiles for a selected agent by monitoring drug efflux from the body of a group of patients for a corresponding multiplicity of target concentrations of the selected agent, said multiplicity of infusion rate profiles including at least a set of profiles which cause the induction of light, average and deep anaesthesia in the patient;
   (ii) determining the body size of the patient, such as their Lean Body Mass;
   (iii) selecting a target concentration of the agent to in turn cause selection from the multiplicity of infusion rate profiles an infusion rate profile substantially corresponding to the infusion rate profile for the selected target concentration;
   (iv) scaling the selected infusion rate profile by the determined body size or Lean Body Mass of the patient; and
   (v) administering the agent to the patient in accordance with the scaled profile by means of an infusion device which is controlled to deliver said agent at said scaled infusion rate profile.

2. The method of claim 1, wherein each said profile is determined by:
   (a) infusing an agent at arbitrary but known rates into a group of patients for each of whom the Lean Body Mass has been determined;
   (b) determining the plasma arterial concentration of the agent in each patient at a number of specific time intervals throughout each infusion period;
   (c) for each patient, estimating the rates of loss of agent from the circulation at a number of specific time instants by dividing the known infusion rates per Lean Body Mass of these instants by the plasma arterial concentrations of the agent at each of these instants;
   (d) calculating the average of the estimated rates of loss of agent from the circulation per Lean Body Mass unit at each specific time interval for the group of patients;
   (e) interpolating the successive average points between the specific time intervals to produce an infusion profile;
   (f) infusing said agent in accordance with said infusion profile determined from said interpolations into a group of patients for each of whom the Lean Body Mass has been determined, said infusion rate being scaled according to said Lean Body mass of each patient; and
   (g) repeating steps (b) to (f) until a desired steady plasma arterial content of the drug is substantially maintained throughout the infusion period.

3. The method of claim 1, wherein said profiles are stored in a data storage and processing device which controls said infusion device at a rate which is subjected to said scaling.

4. The method of claim 2, wherein said profiles are stored in a data storage and processing device which controls said infusion device at a rate which is subjected to said scaling.

5. The method of claim 3, further comprising the step of storage in the storage device of a further multiplicity of similarly determined infusion rate profiles where an anaesthetic agent such as nitrous oxide has been used in addition to the selected anaesthetic agent to induce the desired level of anaesthesia, and selecting one of the profiles where said another agent such as nitrous oxide is used to achieve anaesthesia in the patient.

6. The method of claim 4, further comprising the step of storage in the storage device of a further multiplicity of similarly determined infusion rate profiles where an anaesthetic agent such as nitrous oxide has been used in addition to the selected anaesthetic agent to induce the desired level of anaesthesia, and selecting one of the profiles where said another agent such as nitrous oxide is used to achieve anaesthesia in the patient.

7. The method of claim 1 further comprising, in the case where the stored infusion rate profiles do not correspond to the selected target concentration, the step of calculating the infusion rate by interpolation at each time interval between the rate profile values for target concentrations on either side of the selected target concentration.

8. An infusion system for regulating the delivery of an anaesthetic agent to a patient, including control means for controlling the operation of an infusion pump, said control means including pre-programmed means for varying the infusion rate with respect to elapsed time, said pre-programmed means being programmed with a multiplicity of infusion rate profiles which have been determined by a drug efflux method, and which correspond to a multiplicity of target concentrations of the agent, said multiplicity of infusion rate profiles including at least a set of profiles which cause the induction of light, average and deep anaesthesia in the patient, scaling means for setting the body size or Lean Body Mass of the patient, means for selecting a target concentration to cause selection of the corresponding infusion rate profile so that the pre-programmed means varies the infusion rate in accordance with the corresponding drug infusion rate profile, said scaling means causing modification of the selected pre-programmed infusion rate profile by a fixed proportion over each time period of operation of said infusion pump.

9. The system of claim 8, in which said pre-programmed means is further programmed with a multiplicity of infusion rate profiles which have been determined by a drug efflux method in which a group of patients are administered more than one anaesthetic agent, such as nitrous oxide, to induce the desired level of anaesthesia, and means for selecting one of said profiles where the additional anaesthetic agent such as nitrous oxide is used to achieve anaesthesia in the patient.

* * * * *